United States Patent [19]

Masters et al.

[11] Patent Number: 4,533,651

[45] Date of Patent: Aug. 6, 1985

[54] CATALYSTS FOR OLEFIN OLIGOMERIZATION AND ISOMERIZATION

[75] Inventors: Anthony F. Masters, Diamond Creek; Kingsley J. Cavell, Balwyn, both of Australia

[73] Assignee: Commonwealth Scientific and Industrial Research Organization, Australia

[21] Appl. No.: 548,887

[22] PCT Filed: Feb. 2, 1983

[86] PCT No.: PCT/AU83/00013

§ 371 Date: Oct. 17, 1983

§ 102(e) Date: Oct. 17, 1983

[87] PCT Pub. No.: WO83/02907

PCT Pub. Date: Sep. 1, 1983

[30] Foreign Application Priority Data

Feb. 17, 1982 [AU] Australia .............................. PF2750
Jun. 25, 1982 [AU] Australia .............................. PF4596

[51] Int. Cl.$^3$ .......................... B01J 31/14; B01J 31/22

[52] U.S. Cl. ...................... 502/117; 502/162; 502/167; 502/168; 585/377; 585/378; 585/521; 585/526; 556/19; 556/20; 556/23; 556/13; 556/21; 556/140; 556/14; 556/10; 556/9; 556/40

[58] Field of Search ............... 502/117, 162, 167, 168

[56] References Cited

U.S. PATENT DOCUMENTS

| | | | |
|---|---|---|---|
| 2,969,408 | 1/1961 | Nowlin et al. | 502/117 X |
| 3,485,881 | 12/1969 | Zuech | 502/117 X |
| 3,647,915 | 3/1972 | Bauer et al. | 502/167 X |
| 3,676,523 | 7/1972 | Mason | 502/162 X |
| 3,937,745 | 2/1976 | Wideman et al. | 502/117 X |
| 3,985,677 | 10/1976 | Throckmorton et al. | 502/117 X |
| 3,992,323 | 11/1976 | Yoo et al. | 502/117 |
| 4,118,432 | 10/1978 | Kabanov et al. | 502/117 X |
| 4,176,086 | 11/1979 | Carter | 502/117 X |

*Primary Examiner*—Patrick P. Garvin
*Attorney, Agent, or Firm*—Sughrue, Mion, Zinn, Macpeak, and Seas

[57] ABSTRACT

Catalyst systems for the oligomerization and/or isomerization of olefins which comprise a nickel (II) complex and a co-catalyst. The nickel (II) complex is a square planar species with a trivalent Group V donor ligand, preferably a phosphine or phosphite ligand, a halogen or pseudo-halogen ligand and a bidentate dithio ligand, especially a substituted dithio-$\beta$-diketone ligand.

11 Claims, No Drawings

CATALYSTS FOR OLEFIN OLIGOMERIZATION AND ISOMERIZATION

This invention relates to novel homogeneous and heterogeneous catalysts for the oligomerization and isomerization of olefins and to oligomerization and isomerization processes utilizing such catalysts.

Catalytic dimerization/oligomerization is a useful method for the conversion of moderately cheap lower (e.g. $C_2$–$C_4$) feed olefins into industrially important olefins of higher molecular weight. The use of organometallic complexes in catalysts for this purpose has been widely studied and reported in the literature. [See for example Lefebvre, G. and Chauvin, Y., "*Aspects of Homogeneous Catalysts*", Vol. 1, Ed. Renato Ugo, Chapt. 3, pp. 107–201, 1970; Jolly, P. W. and Wilke, G., "*The Organic Chemistry of Nickel*", Vol. II, Academic Press, 1975; and Bogdanovic, B., "*Advances in Organomet. Chem.*", Vol. 17, 105–140, 1979.]

One such catalyst system is the nickel allyl halide/phosphine/Lewis acid system, various aspects of which have been reviewed by Bogdanovic. (See above.)

Branched products from the dimerization and codimerization or propylene and butylene are suitable as gasoline blending components. Linear products from the dimerization and oligomerization of $C_3$–$C_5$ olefins are desirable for the production of $C_6$–$C_{18}$ plasticizer and detergent range olefins.

The principle objects of the present invention are to provide new catalysts for the dimerization and oligomerization of olefins which give improved turnover numbers (i.e., number of converted substrate molecules per active site on the catalyst) and/or improved selectivity or specificity as to the type or variety of the dimer(s) or oligomer(s) produced from a particular olefin feedstock.

We have now found that such objects can be achieved by the use of catalyst systems which comprise a nickel (II) complex and a co-catalyst. The nickel (II) complex is a square planar species with a trivalent Group V donor ligand, preferably a phosphine or phosphite ligand, a halogen or pseudo-halogen ligand and a bidentate dithio ligand, especially a substituted dithio-β-diketonate ligand.

Thus in accordance with one aspect of the present invention, there is provided a catalyst system for the oligomerization and/or isomerization of olefins which comprises a nickel (II) complex and a co-catalyst (preferably an aluminium alkyl chloride), wherein the nickel (II) complex is a square planar species with a trivalent Group V donor ligand, preferably a phosphine or phosphite ligand, a halogen or pseudo-halogen ligand and a bidentate dithio ligand, especially a substituted dithio-β-diketonate ligand, usually the 2,4-pentanedithionate ligand (commonly abbreviated as "SacSac").

More specifically, the catalysts provided by and/or utilized in the present invention comprise nickel (II) complexes of the formula Ni(R"-RSac-R'Sac)PL$_1$L$_2$L$_3$.X (I)

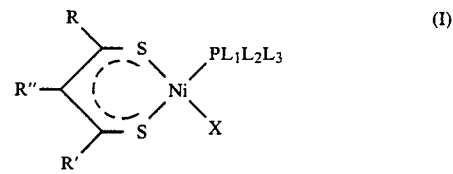

wherein
- R, R' and R" are the same or different groups and each is hydrogen, alkyl, substituted alkyl, alkoxy, substituted alkoxy, phenyl, substituted phenyl, amino, substituted amino, or trihalomethyl;
- each of $L_1$, $L_2$ and $L_3$ is hydrogen or an alkyl group, an alkoxy group, a phenyl group or a phenoxy group, each of which groups may be further substituted; and
- X is a halogen or a pseudo-halogen, such as a nitrate or thiocyanate group.

The alkyl groups or the alkyl moieties of the alkoxy groups may be straight or branched chains.

Substituents on alkyl groups may comprise one or more halo, amino or nitro groups.

Substituents on phenyl groups may include one or more alkyl, alkoxy, nitro, amino or halo groups.

Substituents on amino groups may include one or two alkyl groups or an alkylene group which together with the nitrogen atom form 5- or 6-membered heterocyclic rings which may be further substituted with alkyl groups.

Typically R" is hydrogen and examples of the groups R and R' are methyl, ethyl, t-butyl, methoxy, ethoxy, n-propoxy, n-butoxy, phenyl, trifluoromethyl, amino, pyrrolidyl, piperidyl, and 4-methylpiperidyl.

The compounds of formula (I) are novel, with the exception of the compound in which R=R'=Me; R"=H; L$_1$=L$_2$=L$_3$=Et and X=Cl [see Fackler and Masters, *Inorg. Chem. Acta*, 39, 111 (1980)].

The above air-stable complexes form extremely active olefin dimerization catalysts, when treated with a suitable co-catalyst, as described below. A diversity of activities, stabilities and product distributions dependent upon the groups R, R', R" and L$_1$, L$_2$, L$_3$ have been observed for the catalytic systems derived from the above complexes.

The catalyst systems are generally long-lived and are capable of functioning either in homogeneous solution or in a heterogeneous system when chemically anchored to an insoluble support. The readily varied ligand substituents can be used to control activity and selectivity.

We have also found that the catalyst systems of our invention, in addition to being effective dimerization catalysts, also function as highly active double-bond shift isomerization catalysts. In particular the catalyst systems rapidly isomerize terminal olefins to internal olefins which are much less readily oligomerized. This high isomerization activity may therefore explain why the catalyst systems of our invention show high selectivity towards formation of dimers over higher oligomers.

The co-catalyst may be selected from any of those known per se in the art. As the mode of action of the co-catalyst is not fully understood the types of available co-catalysts cannot be fully specified. Two of probably several possibilities are that it functions by:

(i) generating a nickel hydride species via alkylation and β-elimination, e.g.:

Ni—Cl+Al—Et→Ni—CH₂CH₃+Al—Cl

Ni—CH₂CH₃⇌Ni—H+CH₂=CH₂ or (ii) activation of the nickel via Lewis acid adduct formation, e.g.:

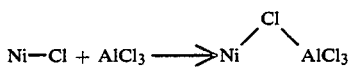

The limiting form of this type of interaction would then be:

Ni⁺AlCl₄⁻

Many of the compounds known generically as "Lewis acids" are useful as co-catalysts. Such compounds include aluminium chloride (AlCl₃) and alkyl aluminium chlorides (e.g., Et₂AlCl), fluoroboranes (e.g., BF₃) and metal chlorides (e.g., TiCl₄).

The catalysts of the present invention may be used in the oligomerization and/or isomerization of olefins or dienes including ethylene, propylene, butene, butadiene, hexene, and mixtures of these.

Thus in accordance with a further aspect of the present invention, there is provided a process for the oligomerization and/or isomerization of olefins which comprises contacting an olefin or a mixture of olefins with a catalyst system as defined above.

The catalysts of the invention may be used in either homogeneous or heterogeneous systems for olefin oligomerization, according to methods generally known per se.

For homogeneous systems the procedure generally involves passing the olefin (if a gas) through a solution of the catalyst in a suitable solvent. It is already known that other propylene dimerization systems are solvent dependent, best results having been obtained in solvents such as chlorobenzene or dichloromethane [G. Lefebvre and Y. Chauvin, *Aspects of Homogeneous Catalysts*, Vol. I, 108, (1970); B. Bogdanovic, B. Spliethoff and G. Wilke, *Agnew., Chem.* (Ger.) 92, 633 (1980)].

In general, therefore, the solvent best suited to any particular catalyst/olefin system will be best determined by experiment. Suitable solvents may be found among the hydrocarbons and halogenated hydrocarbons (both aliphatic and aromatic) and the ethers.

For heterogeneous systems, the nickel complex is supported on a suitable support which will generally be of a type known per se. In some instances, there may be interaction between the catalysts and the support and the support may even function as the co-catalyst. Thus the choice of an appropriate support may be dictated by the type of support-catalyst interaction, i.e., whether the catalyst is adsorbed onto or intercalated within the support, chemically bonded via pendant ligating groups, ion exchanged, and so on. Supporting of inorganic catalysts has been reviewed recently and some possible supports are:
 amorphous silica
 amorphous alumina
 amorphous silica-alumina
 zeolites
 layered silicas
 zirconium phosphates and other layered supports
 functionalized organic polymers
 ion exchange resins.

[See D. C. Bailey and S. H. Langer, *Chem. Rev.*, 81, 109 (1981); F. R. Hartley, P. N. Vezey, *Adv. Organomet. Chem.*, 15, 189 (1977); J. C. Bailar, Jr., *Cat. Rev. Sci. Eng.*, 10, 17 (1974)].

The complex may be supported via the Group V donor ligand, using well established methods, e.g., reaction with a siliconised substrate to give structures of the type:

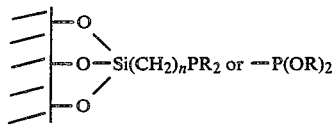

Attachment may also be achieved through the dithio-β-diketone ligand, e.g., by suitable choice of the group R or R″ to allow its attachment to the support.

Several advantages may accrue from the use of supported catalysts, e.g.:

(i) simplication of removal of products from the catalyst, including continuous removal;

(ii) a suitable support may assume the role of co-catalyst as discussed above;

(iii) if the products interfere with catalyst activity then continuous product removal ((i) above) may result in enhanced catalytic activity.

The catalysts of the present invention represent a significant improvement on the prior art. In homogeneous reaction under the conditions of our experiments (described below) the reaction of propylene with examples of the catalytic system is ≧98% selective for dimers. In other systems known to us the dimerization of propylene generally produces 10% or more of higher oligomers. Parallel with the high dimer selectivity of the catalyst system is high activity and a relatively long life-time. Several of the new catalyst systems are, to our knowledge, among the most active published for olefin dimerization and generally have operating lifetimes (with no loss of activity) of ≧six hours.

The invention will be further described with reference to some specific embodiments as set out in the following examples.

EXAMPLE 1

Preparation of Nickel complexes

Although none of the starting materials or final complexes are particularly air or moisture sensitive it was found yields and product purity were improved by carrying out reactions under nitrogen or argon using dry, pure solvents.

The complexes Ni(R″—RSacR′Sac)PL₁L₂L₃ X (I) were prepared by a disproportionation reaction between Ni(R″—RSacR′Sac)₂ and Ni(PL₁L₂L₃)₂X₂ in refluxing benzene, based on the method of Fackler and Masters [Inorg. Chim. Acta, 39, 111 (1980)].

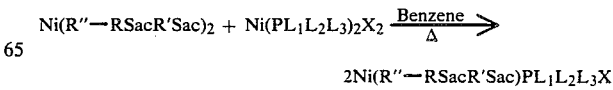

2Ni(R″—RSacR′Sac)PL₁L₂L₃X

The following complexes were prepared in this way:

Ni(SacSac)PEt₃Cl where Et= —CH₂CH₃ and Sac-Sac⁻ =[CH₃C(S)CHC(S)CH₃]⁻
Ni(SacSac)PⁿBu₃Cl where ⁿBu= —CH₂CH₂CH₂CH₃
Ni(SacSac)PPh₃Cl
Ni(SacSac)[Ph₂PCH₂CH₂Si(OEt)₃]Cl
Ni(SacSac)PⁿBu₃Br
Ni(CF₃SacSac)PEt₃Cl where CF₃Sac-Sac=[CF₃C(S)CHC(S)CH₃]⁻
Ni(CF₃SacSac)PⁿBu₃Cl
Ni(ᵗBuSacᵗBuSac)PⁿBu₃Cl where ᵗBuSacᵗ-BuSac⁻ =[(CH₃)₃CC(S)CHC(S)C(CH₃)₃]⁻
Ni(CH₂:CHCH₂—SacSac)PEt₃Cl where CH₂:CHCH₂—Sac-Sac⁻ =[CH₃C(S)C(CH₂CH:CH₂)C(S)CH₃]⁻
Ni(CH₂:CHCH₂—SacSac)PⁿBu₃Cl For the preparation of the complex Ni(Sac-Sac)PPh₃Cl it was found that better yields were obtained if the reflux time was shortened to ¾ hour.

The complex Ni(PhCH₂—SacSac)PⁿBu₃Cl, where PhCH₂—SacSac⁻ =[CH₃C(S)C(CH₂Ph)C(S)CH₃]⁻, was prepared by heating the reactants Ni(PhCH₂—Sac-Sac)₂ and Ni(PⁿBu₃)₂—Cl₂ in toluene at 100°-110° C. for five hours. The hot solution was filtered and the toluene stripped under vacuum. The resulting sticky solid was extracted with 40°-60° petroleum ether and the solution filtered and reduced in volume under vacuum. The solution was then chilled overnight at −20° C. to give the crystalline product.

The starting complexes [Ni(R″—RSacR′Sac)₂ and Ni(PL₁L₂L₃)₂X₂] were prepared by methods described in the literature; Ni(PEt₃)₂Cl₂, Ni(PⁿBu₃)₂Cl₂ and Ni—(PⁿBu₃)₂Br₂ were prepared by the method of Jensen, [Z. anorg. Chem., 229, 265 (1936)], Ni(PPh₃)₂Cl₂ was prepared by the method of Venanzi [J.C.S., 719 (1958)]; Ni(SacSac)₂, Ni(CF₃SacSac)₂, Ni(CH₂:CHCH₂—Sac-Sac)₂ and Ni(PhCH₂—SacSac)₂ were prepared by the method described by Barraclough, Martin and Steward [Aust. J. Chem., 22, 891 (1969)]. Ni(ᵗBuSacᵗBuSac)₂ was prepared following the method of Blejean [Inorg. Nucl. Chem. Letters, 7, 1011 (1971)].

All complexes were characterized by NMR spectroscopy and microanalyses. Microanalysis data for previously unreported compounds are listed in Table 1.

EXAMPLE 2

Preparation of Heterogeneous Catalysts (i) Silica-alumina as support

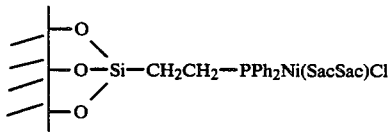

(a) One method used for the preparation of heterogenized catalysts was ligand exchange, carried out by stirring together phosphinated silica-alumina and a toluene solution of Ni(SacSac)PPh₃Cl at room temperature.

The phosphinated support was prepared by the method of Czakova and Capka [J. Molecular Catalysis, 11, 313 (1981)], and contained 0.43% phosphorous.

To prepare the supported complex: 1 g of the phosphinated support was loaded into a Schlenk tube under argon and 0.105 g of Ni(SacSac)PPh₃Cl was loaded into a second tube under argon and dissolved in 20 ml of dry, degassed toluene. This solution was added in small aliquots (about 2 or 3 ml) to the support with constant stirring. The colour of the solution over the support was allowed to fade before the next aliquot was added. The support was then stirred a further two hours in the presence of excess complex. The excess nickel complex and solvent were removed by decantation and the support washed with 20×10 ml aliquots of toluene by decantation. The final washings were colourless and the support was now deep red/purple in colour. The support and complex were then dried under vacuum (10⁻³τ) at 50° C. for three hours. (Table 2).

(b) A second method employed for the preparation of a supported catalyst was the interaction of the support material with a nickel complex containing a phosphine with a reactive functional group suitable for reacting with the hydroxyl groups on the support.

The complex Ni(SacSac)[Ph₂PCH₂CH₂Si(OEt)₃]Cl, prepared as described in Example 1, was reacted with silica-alumina (dried by heating at 250°-300° C. under a vacuum of 10⁻³τ for two hours) in refluxing benzene or toluene. The deep purple solid that was obtained was filtered and washed with fresh solvent (benzene or toluene) and then extracted in a continuous extraction apparatus with refluxing solvent. The resulting solid was then dried under vacuum (10⁻³τ) for three hours at 50° C. (Table 2 lists the conditions used for the preparation of complexes supported on silica-alumina.)

(ii) Polystyrene beads as support

Catalysts supported on polystyrene beads were prepared by phosphine exchange, which occurred when phosphinated polystyrene beads were treated with a solution of Ni(SacSac)PPh₃Cl in tetrahydrofuran (THF).

Highly crosslinked (>50%) Amberlite XAD-4 polystyrene beads (20–60 mesh, 725 m²g⁻¹ surface area) were thoroughly washed, by the method recommended by Pittman and Wilemon [J. Org. Chem., 46, 1901 (1981)]. After washing the resin was filtered and dried in vacuo at 25° C. A portion of the dried beads (20 g) was suspended in CCl₄ (300 ml) and brominated by the method of Pittman and Wilemon. The straw coloured brominated beads were dried in vacuo at room temperature for 24 hours ready for further treatment. Microanalysis indicated the beads contained 22.8% (w/w) bromine, i.e., approximately 40% of the polystyrene rings were brominated.

Brominated beads (4.5 g) were then phosphinated as described by Relles and Schluenz [J.A.C.S., 96, 6469 (1974)]. The white to pale-yellow phosphinated beads were thoroughly dried under vacuo and stored under argon.

To support the nickel complex on the resin the following procedure was used. Phosphinated beads (ca. 1–2 g) were loaded into a Schlenk tube, under argon and slurried with dry, degassed THF (ca. 5 ml). Ni(Sac-Sac)PPh₃Cl was loaded into a second Schlenk tube under argon and then dissolved in pure THF (ca. 10 ml). This solution was then added in small aliquots to the phosphinated resin and the mixture stirred after each addition until the supernatant was colourless. The supernatant was decanted from the resin after each aliquot to remove displaced, free PPh₃; thus reducing the likelihook of the back exchange reaction occurring. This procedure was continued until all the nickel complex had been loaded onto the beads or until the uptake of Ni(SacSac)PPh3Cl ceased. The beads were then thoroughly washed with THF (5×10 ml) and dried in vacuo for 12 hours at room temperature to give deep red/purple coloured beads. In one example where an excess of phosphinated beads were used NMR analysis of the residue from the combined decanted solvent fractions and washings indicated only free PPh3. Approximately 80% of the expected PPh3 was recovered.

The beads were analyzed for nickel content.

| Sample No. | % Ni (w/w) |
|---|---|
| TM82-1-47 | 0.19 |
| TM82-1-48 | 0.47 |

EXAMPLE 3

Homogeneous Catalysis

All apparatus was carefully dried and all solvents and chemicals purified using standard procedures. Solvents were dried and degassed before use. Gas feeds were C.P. grade and were passed through 3 Å molecular sieves before reaction. Where necessary, manipulations were carried out under dry, oxygen-free argon.

The apparatus consisted of a 500 ml 3-necked round-bottom flask fitted with a gas bubbler and a rubber septum; the third neck was stoppered. Before proceeding with experiments the apparatus was filled with purified argon.

Dry oxygen free toluene (ca. 50 g) was transferred under argon into the reaction vessel. The vessel and contents were cooled in a bath maintained at $-15°\pm2°$ C. Dry propylene was bubbled through the solution at a constant inlet flow rate, approximately 150 ml/minute. This gas flow was maintained throughout the entire duration of the experiment. 20-30 Minutes from the commencement of the passage of gas, to allow saturation of the toluene with gas, co-catalyst (Et$_2$AlCl, approx. 0.1-0.15 ml) was added by syringe. Sixty minutes after the addition of the co-catalyst an aliquot of the solution was taken for analysis as a pre-run blank. After a further ten minutes a solution of the nickel complex, Ni(SasSac)(PPh3)Cl(0.0122 g, 2.50×10$^{-5}$ mol in 5-10 g toluene) was transferred under argon to the mixture. Aliquots were taken from the reaction mixture at various periods during the experiment, deactivated by shaking with dilute aqueous hydrochloric acid, and then analyzed by gas chromatography (G.C.).

Results from the experiment are listed in Table 3.

A blank experiment, i.e., without the nickel complex, was carried out under the same conditions as those employed in the catalytic experiment above. This was done to check what effect, if any, the co-catalyst (Et$_2$AlCl) may have had on the dimerization of propylene.

Aliquots were taken at various times, deactivated as before and injected into the G.C. Under the conditions employed no dimerization or oligomerization of propylene was detectable after four hours of operation.

According to the commonly accepted mechanism for the transition metal catalysed olefin oligomerization reaction there are twelve possible C$_6$ isomers obtained directly or by double-bond shift isomerization. Of these we observe and can identify ten (by G.C.M.S. analysis and with the use of standards). The remaining two are probably present in amounts too small to be observable or are obscured by other peaks in the G.C. trace.

It is evident from Table 3 that the activity of this catalyst drops with time. The catalyst has a half-life of approximately thirty minutes.

EXAMPLES 4-10

The following examples show the effects of varying the dithio-$\beta$-diketonate and phosphine ligands on catalyst activity and product distribution. The same method of catalyst testing as discussed in Example 3 was employed in each case. Et$_2$AlCl was the co-catalyst in each experiment, propylene was the feed gas and toluene the solvent. Catalysts were tested for periods over four hours and up to six hours and all experiments were repeated at least once. These catalysts were found to be quite stable under the conditions of the experiments, no deactivation of the catalyst with time, as observed in Example 3, was detected.

Tables 4 and 5 show the effects of changing the ligands on catalyst activity and product distribution respectively. Results from Example 3 are also included in the Tables for comparison.

EXAMPLES 11 AND 12

Examples 11 and 12 show the effects that changing the solvent has on the catalytic system. In these examples the solvent used was chlorobenzene. The same conditions and procedures for testing, as described in Examples 3-10, were employed. Propylene was the feed olefin. The main observation arising from the change to the more polar chlorobenzene was the large increase in the catalysts' turnover numbers compared with the same catalysts in toluene; a four-to five-fold increase was observed, c.f. Examples 4 and 5 in Table 4. Results for Examples 11 and 12 are given in Table 6.

EXAMPLE 13

In this example a representative catalyst, Ni—(SacSac)P$^n$Bu$_3$Cl, was employed to test the oligomerization of ethylene.

The same procedure as given in Example 3 was followed except the nickel complex used was Ni(SacSac)—P$^n$Bu$_3$Cl and the feed gas was ethylene. A gas flow rate of 250 ml/minute was employed. Toluene was used as the solvent and Et$_2$AlCl was the co-catalyst.

On the gas outlet side of the apparatus a cold trap was fitted (held at $-68°$ C.) to trap out any volatile products carried through by the ethylene.

The catalyst was tested over a three hour period and was found to have a turnover number of ca. 11,700 mol of ethylene converted (mol Ni)$^{-1}$ hr$^{-1}$, which is approximately twice that obtained with a propylene feed—see Example 5, Table 4.

The product distribution after three hours operation was as follows:
 1.8% 1-butene
 75.7% trans-2-butene
 21.6% cis-2-butene
 0.9% C$_6$ products
 no oligomers above C$_6$ were observed.

The change in butene distribution with time is given in Table 7. The catalytic double-bond shift isomerization behaviour of these catalysts can be clearly seen from this Table.

Isomerization

EXAMPLE 14

From our experiments it was evident that rapid double-bond shift isomerization of olefins with more than three carbon atoms was occurring. This can be clearly seen in Table 7.

To follow this process the isomerization of 1-hexene was undertaken.

1-Hexene (analyzed as 97.8% 1-hexene, 2.2% cis-3-hexene) was freshly distilled from sodium under nitrogen. All operations were carried out under an atmosphere of nitrogen. The purified 1-hexene (5 g) was dissolved in 42 g of pure, dry toluene at $-15°$ C. Co-catalyst, $Et_2AlCl$, was added and the solution stirred at $-15°$ C. for one hour. After this time an aliquot was withdrawn, as a pre-run blank, and analyzed by G.C. (No isomerization or oligomerization was detected.) A toluene solution of $Ni(SacSac)P^nBu_3Cl$ (0.3104 g, $2.4315 \times 10^{-5}$ mol $Ni(SacSac)P^nBu_3Cl$ in 5 g toluene) was then added and aliquots were periodically withdrawn, deactivated (with 0.1M HCl) and analyzed by G.C. Results from the isomerization experiment are given in Table 8. There was no detectable hexene oligomerization under the conditions of this experiment.

EXAMPLE 15

In this experiment 1-hexene was added to a catalyst that was already oligomerizing propylene. This was done to establish whether there was any observable interference in the isomerization process caused by the oligomerization reaction, or whether isomerization is competitive with oligomerization under the conditions of our experiments.

Propylene was oligomerized by the method discussed in Example 3 using $Ni(SacSac)P^nBu_3Cl$ with $Et_2AlCl$ as the catalyst system and toluene as solvent. After 240 minutes of operation (the expected catalyst turnover number and product distribution having been observed) 5 ml of pure, dry 1-hexene was added to the system by syringe. An aliquot was taken five minutes after the 1-hexene addition, deactivated with 0.1M HCl and analyzed by G.C. The following distribution of hexene isomers was detected:

- 1-hexene: (too little to be detectable in the presence of the 2,3-dimethyl-1-butene and cis-4-methyl-2-pentene produced in the dimerization of propylene.)
- trans-2-hexene: 65.2%
- cis-2-hexene: 23.8%
- cis-3-hexene: 1.4%
- trans-3-hexene: 9.6%

From the results it can be seen that the isomerization of 1-hexene to the various internal olefins is still extremely rapid in the presence of propylene. It is evident the isomerization reaction is competitive with and probably preferred to oligomerization. It is possible that the isomerization of the trans- internal olefins to their cis-counterparts has been slowed by the oligomerization process. However, the presence of the various hexene isomers produced separately in the dimerization of propylene make any conclusion drawn from the relative amounts of the internal olefin isomers uncertain.

Heterogeneous Catalysis

EXAMPLES 16-19

These examples show that representatives of the complexes (I), when heterogenized by chemical attachment to a support (both organic and inorganic support materials being used) by the methods given in Example 2 and when activated in the normal manner, are active oligomerizations and isomerization catalysts.

In Examples 16-18 the same apparatus, conditions and procedures as employed in Example 3 for the homogeneous system were used. Propylene was the feed olefin, and toluene the solvent. However, at the appropriate time (approximately sixty minutes after the addition of co-catalyst, and after removal of the pre-run blank) the solid heterogenized catalyst was added under pure, dry argon via a solids transfer tube (0.3 to 0.9 g of solid sample was added, depending on the percentage of Ni present). Thus a three phase system was obtained. Aliquots were taken at various intervals and analyzed by G.C. Results for Examples 16-18 are presented in Tables 9 and 10. All heterogeneous systems tested showed undiminished activity after five hours of operation.

It is evident from these examples (Table 9) that heterogenized complexes give rise to active catalysts. In particular the catalyst in Example 18, prepared in the manner described in Example 2(i)(b), has an activity comparable to the less active of the homogeneous catalysts.

Substantial phosphine oxide formation has been shown to accompany the reaction of $(EtO)_3SiCH_2CH_2PPh_2$ with silica [see Bemi, Clark, Davies, Fyfe and Wasylishen, J.A.C.S., 104, 438 (1982)]. Significantly the supported complex prepared in this manner (as described in Example 2(i)(a)) gives rise to a substantially less active catalyst (Example 17).

The catalyst tested in Example 16 is supported on highly crosslinked (>50%) polystyrene. The low activity of the catalyst may derive from diffusion limitations on reagent penetration of the highly crosslinked resin under the experimental conditions.

A comparison of the product distributions for heterogeneous (Examples 16 and 18, Table 10) and homogeneous (Examples 3 to 10, Table 5) catalysts shows significant differences. Heterogeneous systems give rise to a greater amount of less-branched products, in particular there is a large increase in the percentage of methylpentenes produced, at the expense of the more highly branched dimethylbutenes. This feature is consistent with the support exerting ligand-effects of a steric nature on the catalyst. It is predicted from the generally accepted mechanism for olefin oligomerization that sterically demanding ligands would lead to a buildup of methylpentenes among the $C_6$ products. [Bogdanovic, "Advances in Organomet. Chem.", Vol. 17, 105-140 (1979).]

Example 19 was carried out to establish whether the integrity of the heterogenized catalyst was retained during catalysis or whether catalyst was leached (in part or in full) from the support during operation. In this experiment the supported sample KCSup6, Table 2 was tested in the normal manner using the same apparatus, conditions and procedure as previously described. Propylene was the feed olefin and toluene the solvent. Aliquots were taken at intervals and analyzed in the usual way. After two hours operation the supernatant was removed from the still highly coloured solid and transferred to a second reaction vessel held at $-15°$ C. (The solid and reaction vessel were stored at $-20°$ C. until required.) Whilst maintaining the temperature of the vessel and supernatant at $-15°$ C. the flow of pure propylene was restored and the system operated as in a normal test experiment. After ninety minutes of operation an aliquot was taken and analyzed. No increase in the amount of oligomers over that present in the solution when the solid material was removed was detected. Thus no detectable activity resided with the liquid phase, i.e., no active catalyst was leached from the support.

The solid heterogenized catalyst was brought to −15° C. and washed three times with 15 ml. aliquots of cold, degassed, dry toluene and the washings discarded. Cold (−15° C.) toluene (42 g) and a small amount of co-catalyst (Et$_2$AlCl; 0.05 ml) were added to the solid and the propylene flow re-initiated. Aliquots were removed for analysis five minutes and 145 minutes after the passage of propylene was recommenced.

Results for each stage of the experiment, Example 19, are given in Table 11.

Table 11 shows that within experimental error all catalytic activity for propylene oligomerization is associated with the solid supported catalyst. No activity has been lost by catalyst leaching or by other processes, i.e., the nickel-phosphorous bond remains intact throughout the catalyst initiation and operation.

TABLE 1

Microanalysis Data for Nickel Complexes

| Complex | Elemental Analysis (%) (Calculated) | | | | | |
|---|---|---|---|---|---|---|
| | C | H | S | P | Cl/Br | F |
| Ni(CH$_2$:CHCH$_2$—SacSac)$_2$ | 47.61 | 5.37 | 31.7 | — | — | — |
| | (47.89) | (5.53) | (31.96) | | | |
| Ni(PhCH$_2$—SacSac)$_2$ | 56.93 | 5.51 | 25.3 | — | — | — |
| | (57.49) | (5.23) | (25.58) | | | |
| Ni(SacSac)PPh$_3$Cl | 56.68 | 4.57 | 12.7 | 6.4 | 7.1 | — |
| | (56.64) | (4.55) | (13.15) | (6.35) | (7.27) | |
| Ni(SacSac)P$^n$Bu$_3$Cl | 48.05 | 7.97 | 14.5 | 7.24 | 8.5 | — |
| | (47.74) | (8.01) | (14.99) | (7.4) | (8.29) | |
| Ni(CF$_3$SacSac)P$^n$Bu$_3$Cl | 42.18 | 6.54 | 13.0 | 6.8 | 7.2 | 11.9 |
| | (42.39) | (6.49) | (13.31) | (6.43) | (7.36) | (11.83) |
| Ni($^t$BuSac$^t$BuSac)P$^n$Bu$_3$Cl | 53.88 | 8.84 | 12.8 | 6.0 | 7.1 | — |
| | (53.97) | (9.06) | (12.53) | (6.05) | (6.93) | |
| Ni(CH$_2$:CHCH$_2$—SacSac)PEt$_3$Cl | 44.06 | 6.70 | 16.9 | 7.9 | 9.0 | — |
| | (43.83) | (6.83) | (16.72) | (8.07) | (9.24) | |
| Ni(CF$_3$SacSac)PEt$_3$Cl | 33.47 | 5.20 | 15.4 | 7.79 | 7.7 | 14.34 |
| | (33.24) | (4.82) | (16.13) | (8.1) | (8.92) | (13.9) |
| Ni(PhCH$_2$—SacSac)P$^n$Bu$_3$Cl | 55.36 | 7.66 | 12.7 | 6.1 | 6.9 | — |
| | (55.67) | (7.79) | (12.38) | (5.98) | (6.85) | |
| Ni(SacSac)P$^n$Bu$_3$Br | 43.57 | 6.98 | 13.3 | 6.7 | 16.9 | — |
| | (43.24) | (7.26) | (13.58) | (6.56) | (16.92) | |

TABLE 2

Preparation of Supported Catalysts
Reaction Conditions

| Catalyst No. | Weight complex (g)/weight support (g) | Solvent (Volume)/ reflux time | Extraction time | % Ni |
|---|---|---|---|---|
| KCSup 4 | 0.25/2.5 | benzene (30 ml)/24 hours then toluene (30 ml)/2 hours | washed only, 20 × 10 ml toluene | 0.54% |
| KCSup 5 | 0.22/2.5 | toluene (50 ml)/5 hours | 2 hours | 0.43% |
| KCSup 6 | 0.40/2.7 | benzene (30 ml)/4 hours | 3 hours | 0.37% |
| KCSup 1 | Prepared by phosphine exchange at room temperature, followed by thorough washing. | | | 0.24% |
| KCSup 2 | | | | 0.24% |

TABLE 3

Data from the Oligomerization of Propylene with the Complex Ni(SacSac)PPh$_3$Cl

| Time aliquots taken after catalyst addition (min.) | Turnover Number [mol C$_3$H$_6$ reacted (mol Ni)$^{-1}$hr$^{-1}$] | Product Distribution (%) | |
|---|---|---|---|
| 5 | 22000 | Dimethyl-butenes | 10 |
| 15 | 12400 | Methyl-pentenes | 74 |
| 30 | 7900 | Hexenes | 16 |
| 65 | 4700 | Higher oligomers | Only dimers were detected. |
| 120 | 3600 | | |
| 185 | 2900 | | |

TABLE 4

Effects of Changing Ligands on Catalyst Activity

| Example number | Catalyst | Turnover number [mol C$_3$H$_6$ converted (mol Ni)$^{-1}$ hr$^{-1}$] |
|---|---|---|
| 4 | Ni(SacSac)PEt$_3$Cl | 3,500 |
| 5 | Ni(SacSac)P$^n$Bu$_3$Cl | 6,000 |
| 6 | Ni(CF$_3$SacSac)P$^n$Bu$_3$Cl | 13,000 |
| 7 | Ni(CH$_2$:CHCH$_2$—SacSac)PEt$_3$Cl | 4,000 |
| 8 | Ni(CH$_2$:CHCH$_2$—SacSac)P$^n$Bu$_3$Cl | 2,200 |
| 9 | Ni($^t$BuSac$^t$BuSac)P$^n$Bu$_3$Cl | 21,300 |
| 10 | Ni(PhCH$_2$—SacSac)P$^n$Bu$_3$Cl | 5,800 |
| 3 | Ni(SacSac)PPh$_3$Cl | 22,000* |

*After 5 minutes of operation. This catalyst rapidly deactivates; it has an operational half-life of approximately 30 minutes.

TABLE 5
Effects of Changing Ligands on Product Distribution

| | | Product Distribution % | | | |
|---|---|---|---|---|---|
| | | C$_6$ Products | | | |
| Example number | Catalyst | Dimethyl-butenes | Methyl-pentenes | Hexenes | Higher oligomers |
| 4 | Ni(SacSac)PEt$_3$Cl | 26 | 67 | 7 | 1-2 |
| 5 | Ni(SacSac)P$^n$Bu$_3$Cl | 29 | 67 | 4 | 4-5 |
| 6 | Ni(CF$_3$SacSac)P$^n$Bu$_3$Cl | 26 | 69 | 5 | 2 |
| 7 | Ni(CH$_2$:CHCH$_2$—SacSac)PEt$_2$Cl | 24 | 70 | 6 | — |
| 8 | Ni(CH$_2$:CHCH$_2$—SacSac)P$^n$Bu$_3$Cl | 25 | 69 | 6 | <1 |
| 9 | Ni($^t$BuSac$^t$BuSac)P$^n$Bu$_3$Cl | 27 | 69 | 4 | 2 |
| 10 | Ni(PhCH$_2$—SacSac)P$^n$Bu$_3$Cl | 28 | 69 | 3 | — |
| 3 | Ni(SacSac)PPh$_3$Cl | 10 | 74 | 16 | — |

TABLE 6
Catalyst Activity with Chlorobenzene as Solvent

| Example No.* | Catalyst | Turnover Number [mol C$_3$H$_6$ converted (mol Ni)$^{-1}$ hr$^{-1}$] |
|---|---|---|
| 11 | Ni(SacSac)PEt$_3$Cl | 18,000 |
| 12 | Ni(SacSac)P$^n$Bu$_3$Cl | 22,000 |

*The product distributions in Examples 11 and 12 are the same as those given for the same catalysts in toluene, see Examples 4 and 5.

TABLE 7
Change in Butene Distribution with Time in the Oligomerization of Ethylene

| Butene isomer | Sampling Time (min) | | | | | |
|---|---|---|---|---|---|---|
| | 5 | 15 | 30 | 60 | 120 | 180 |
| 1-butene | 51.4 | 27.1 | 11.6 | 3.6 | 1.6 | 1.8 |
| trans-2-butene | 34.0 | 47.8 | 61.4 | 69.8 | 76.0 | 76.4 |
| cis-2-butene | 14.6 | 25.1 | 27.1 | 26.6 | 22.4 | 21.8 |
| | % of Each Butene | | | | | |

TABLE 8
Isomerization of Hexene

| Hexene isomer | Sampling Time (min) | | | | | |
|---|---|---|---|---|---|---|
| | 5 | 15 | 30 | 60 | 120 | 180 |
| 1-hexene | 4.0 | 1.8 | 1.6 | 1.2 | 1.1 | 0.7 |
| trans-2-hexene | 36.7 | 46.7 | 55.3 | 65.7 | 70.4 | 72.3 |
| cis-2-hexene | 54.5 | 46.6 | 36.7 | 24.0 | 16.7 | 15.2 |
| cis-3-hexene | 2.0 | 2.1 | 2.1 | 2.0 | 2.0 | 1.9 |
| trans-3-hexene | 2.8 | 2.8 | 4.3 | 7.1 | 9.8 | 9.9 |
| | % of Each Hexene | | | | | |

TABLE 9
Activity of Heterogenized Catalysts

| Example No. | Catalyst No. | Catalyst and support | Turnover Number [mol C$_3$H$_6$ converted (mol Ni)$^{-1}$ hr$^{-1}$] |
|---|---|---|---|
| 16 | TM82-1-47 (0.19 wt. % Ni) | Ni(SacSac)Cl.PPh$_2$—XAD—4 polystyrene beads | 350 |
| 17 | KCSup 1 (0.24 wt. % Ni) | Ni(SacSac)Cl.PPh$_2$CH$_2$CH$_5$Si—O— on silica-alumina | 25 |
| 18 | KCSup 6 (0.37 wt. % Ni) | Ni(SacSac)Cl.PPh$_2$CH$_2$CH$_2$Si—O— on silica-alumina | 2500 |

TABLE 10
Product Distribution for Heterogenized Samples

| | | Product Distribution % | | | |
|---|---|---|---|---|---|
| | | C$_6$ products | | | |
| Example No. | Catalyst | Dimethyl-butenes | Methyl-pentenes | Hexenes | Higher oligomers |
| 16 | Ni(SacSac)Cl.PPh$_2$—XAD—4 polystyrene beads | 10 | 82 | 8 | 4 |
| 17 | Ni(SacSac)Cl.PPh$_2$CH$_2$CH$_2$Si— on silica-alumina | | Not analysed | | |
| 18 | Ni(SacSac)Cl.PPh$_3$CH$_2$CH$_2$Si— on silica-alumina | 8 | 83 | 9 | 7 |

TABLE 11

Data from Testing the Stability of Heterogenized Catalysts

|  | Total C$_3$H$_6$ converted* (mol) | Turnover number of catalyst [mol C$_3$H$_6$ converted (mol Ni)$^{-1}$ hr$^{-1}$] |
|---|---|---|
| System before separation of supernatant and solid (after 120 min. operation) | 0.2760 | 2500 |
| Supernatant only (90 minutes after recommencement of propylene flow) | 0.2752+ | 0 |
| solid catalyst | | |
| (5 min. after recommencement) | 0.0102 | 2500 |
| (145 min. after recommencement) | 0.2740 | 2300 |

*Calculated from the total number of dimers and higher oligomers present in solution as determined from G.C. analysis.

+N.B. the supernatent contains all oligomers produced in the first stage of the experiment. The figure in the table shows that no further amounts of propylene have been oligomerized.

We claim:

1. In a catalyst system for the oligomerization and/or isomerization of olefins which comprises a nickel (II) complex and co-catalyst, the improvement wherein the nickel (II) complex is a square planar species with a trivalent Group V donor ligand, a halogen or pseudo-halogen ligand and a dithio-β-diketone ligand which may be substituted with one or more non-deleterious groups.

2. A catalyst as claimed in claim 1, characterized in that the Group V donor ligand is a phosphine or phosphite ligand.

3. The catalyst system of claim 1, wherein the nickel complex is a compound of the formula I

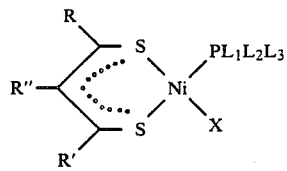

wherein

R, R' and R'' are the same or different groups and each is hydrogen, alkyl, substituted alkyl, alkenyl, substituted alkenyl, alkoxy, substituted alkoxy, phenyl, substituted phenyl, amino, substituted amino, or trihalomethyl; L$_1$, L$_2$ and L$_3$ are the same or different groups and each is hydrogen or an alkyl group, alkoxy group, a phenyl group or a phenoxy group, each of which groups may be further substituted with non-deleterious groups; and X is a halogen or a pseudo-halogen.

4. The catalyst system of claim 3, wherein the pseudo-halogen is a nitrate or thiocyanate group.

5. The catalyst system of claim 3 or claim 4, wherein the substituents on alkyl or alkenyl groups, when present, comprise one or more halo, amino, phenyl or nitro groups.

6. The catalyst system of claim 3 wherein the substituents on the phenyl groups, when present, comprise one or more alkyl, alkoxy, nitro, amino or halo groups.

7. The catalyst system of claim 3 wherein the substituents on the amino groups, when present, comprise one or two alkyl groups, or an alkylene group which together with the nitrogen atom forms a 5- or 6-membered heterocyclic ring which may be further substituted with alkyl groups.

8. The catalyst system of claim 3, wherein in formula (I) the groups R and R' are selected from methyl, ethyl, t-butyl, methoxy, ethoxy, n-propoxy, n-butoxy, phenyl, trifluoromethyl, amino, pyrrolidyl, piperidyl, and 4-methylpiperidyl.

9. The catalyst system of claim 1 or claim 3, characterized in that the cocatalyst is an aluminium alkyl chloride.

10. The catalyst system of claim 1 or claim 3, characterized in that the system is homogeneous and comprises a solution of the complex and the co-catalyst, if used, in a suitable solvent.

11. The catalyst system of claim 1 or claim 3, characterized in that the system is heterogeneous and the complex is attached to a suitable support.

* * * * *